(12) United States Patent
Delfrate et al.

(10) Patent No.: US 12,077,559 B2
(45) Date of Patent: Sep. 3, 2024

(54) PROCESS FOR THE PREPARATION OF 3α-HYDROXY-5α-PREGNAN-20-ONE (BREXANOLONE)

(71) Applicant: INDUSTRIALE CHIMICA S.R.L, Milan (IT)

(72) Inventors: Claudio Delfrate, Rho (IT); Davide Rigamonti, Erba (IT); Tea Borelli, Como (IT); Roberto Lenna, S. Giorgio su Legnano (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 763 days.

(21) Appl. No.: 17/282,772

(22) PCT Filed: Oct. 21, 2019

(86) PCT No.: PCT/EP2019/078580
§ 371 (c)(1),
(2) Date: Apr. 4, 2021

(87) PCT Pub. No.: WO2020/083839
PCT Pub. Date: Apr. 30, 2020

(65) Prior Publication Data
US 2021/0388020 A1   Dec. 16, 2021

(30) Foreign Application Priority Data

Oct. 22, 2018 (IT) .......................... 102018000009683

(51) Int. Cl.
  *C07J 7/00*  (2006.01)
  *C07J 17/00*  (2006.01)
  *C07J 33/00*  (2006.01)
(52) U.S. Cl.
  CPC .............. *C07J 7/002* (2013.01); *C07J 17/00* (2013.01); *C07J 33/002* (2013.01)
(58) Field of Classification Search
  CPC ....................................................... C07J 7/00
  See application file for complete search history.

(56) References Cited

U.S. PATENT DOCUMENTS 5,795,982 A    8/1998  Geurts et al.
2014/0158079 A1  2/2014  Guy et al.

FOREIGN PATENT DOCUMENTS

| CN | 1821263 A | 8/2006 |
| EP | 2688902 B1 | 1/2014 |
| GB | 442319 | 12/1934 |

OTHER PUBLICATIONS

Fishman, "Conversion of ketones to olefins." Journal of Organic Chemistry, 28, 1443-4 1963.*
Campos Neves et al., "Improved syntheses of aromatase inhibitors and neuroactive steroids efficient oxidations and reductions at key positions for bioactivity", Tetrahedron, 1999, 55, 3255-64.*
Hitchin "A novel scalable and stereospecific synthesis of 3a- and 3b-amino-5a-androstan-17-ones and 3a- and 3b-amino-5a-pregnan-20-ones" Tetrahedron Letters 53 (2012) 2868-2872.*
Sun "Highly efficient chemoselective deprotection of O,O-acetals and O,O-ketals catalyzed by molecular iodine in acetone." J. Org. Chem. 2004, 69, 8932-8934.*
Kondritzer "Investigation of Methyl Pyridinium-2-aldoxime Salts" Journal of Pharmaceutical Sciences vol. 50, No. 2, Feb. 1961, 109-112.*
Search Report dated Jan. 19, 2021 for corresponding Italian patent application No. 102020000007180.
Macnevin, Christopher J., et al. "Development and screening of water-soluble analogues of progesterone and allopregnanolone in models of brain injury." Journal of medicinal chemistry 52.19 (2009): 6012-6023.

(Continued)

*Primary Examiner* — David K O'Dell
(74) *Attorney, Agent, or Firm* — Leason Ellis LLP

(57) ABSTRACT

The present invention relates to a new process for the synthesis of 3α-hydroxy-5α-pregnan-20-one, commonly known as brexanolone, wherein the corresponding cyclic 20-ketal or cyclic 20-thioketal compound of formula (IV) is deprotected with the use or iodine in an organic solvent: (I).

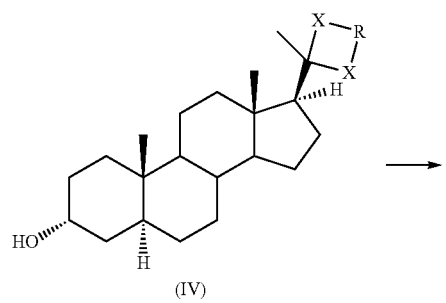

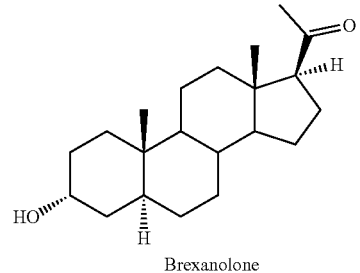

11 Claims, 4 Drawing Sheets

(56) References Cited

OTHER PUBLICATIONS

Das, S., Borah R., Devi R. R., & Thakur A. J. (2008). Molecular iodine in protection and deprotection chemistry. Synlett, 2008(18), 2741-2762.

Wiebe J. P., Deline C., Buckingham K. D., Dave V., & Stothers J. B. (1985). Synthesis of the allylic gonadal steroids, 3α-hydroxy-4-pregnen-20-one and 3α-hydroxy-4-androsten-17-one, and of 3α-hydroxy-5α-pregnan-20-one. Steroids, 45(1), 39-51.

Purdy R. H., Morrow A. L., Blinn J. R., & Paul S. M. (1990). Synthesis, metabolism, and pharmacological activity of 3. alpha.-hydroxy steroids which potentiate GABA-receptor-mediated chloride ion uptake in rat cerebral cortical synaptoneurosomes. Journal of medicinal chemistry, 33(6), 1572-1581.

Neves Andres Campos et al "Improved syntheses of aromatase inhibitors and neuroactive steroids efficient oxidations and reductions at key positions for bioactivity." Tetrahedron 55.11 (1999): 3255-3264.

* cited by examiner

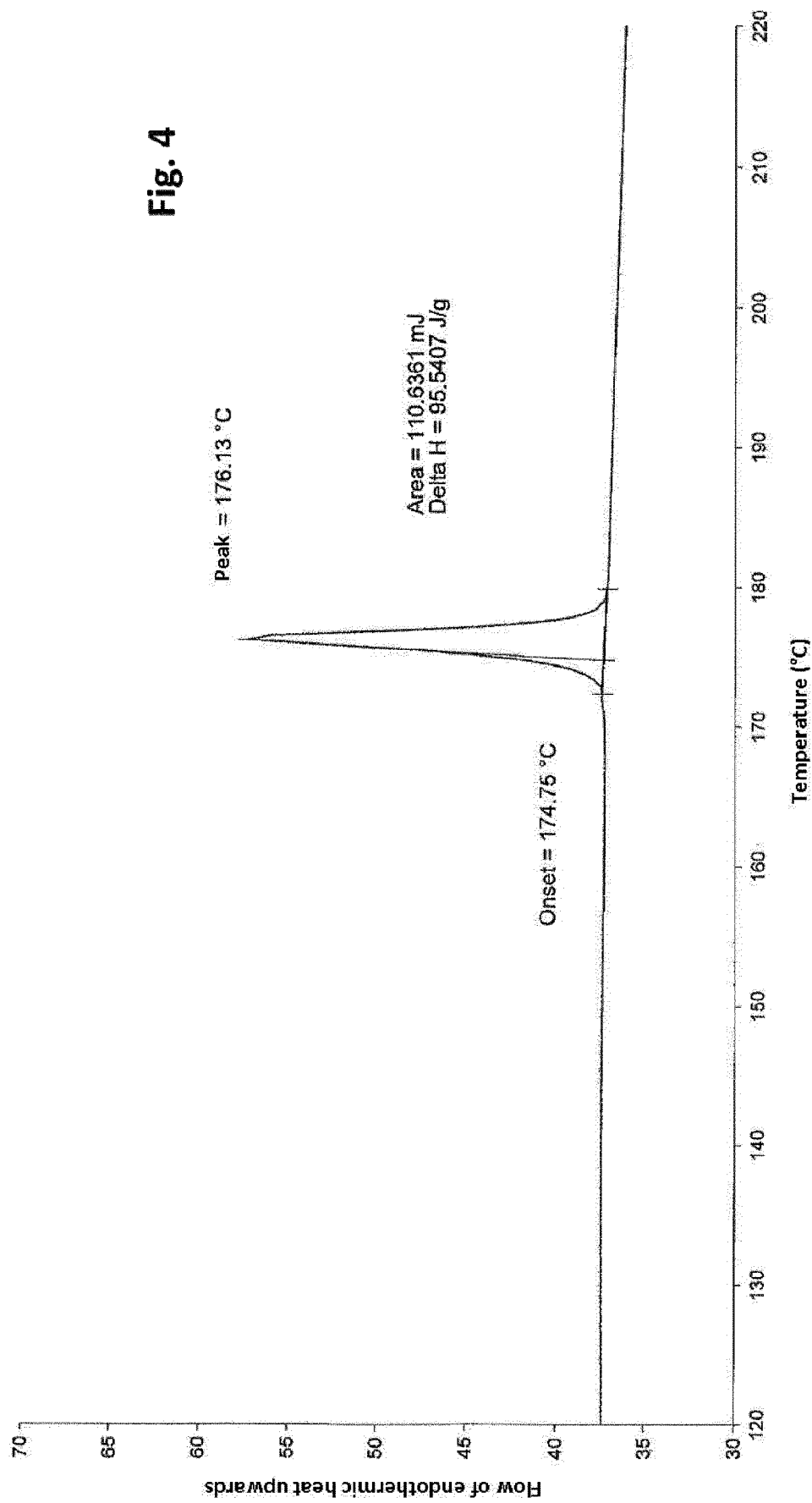

PROCESS FOR THE PREPARATION OF 3α-HYDROXY-5α-PREGNAN-20-ONE (BREXANOLONE)

CROSS REFERENCE TO RELATED APPLICATIONS

This application is a national phase of PCT application No. PCT/EP2019/078580, filed Oct. 21, 2019, which claims priority to IT patent application No. 102018000009683, filed Oct. 22, 2018, all of which are incorporated herein by reference thereto.

FIELD OF THE INVENTION

The present invention relates to the field of processes for the synthesis of active ingredients for pharmaceutical use, and in particular to a process for the industrial-scale preparation of 3α-hydroxy-5α-pregnan-20-one, an active ingredient useful for the therapy of postpartum depression. The compound is also known by the name of allopregnanolone or by the USAN name brexanolone, which will be used in the rest of the text, and has the following formula:

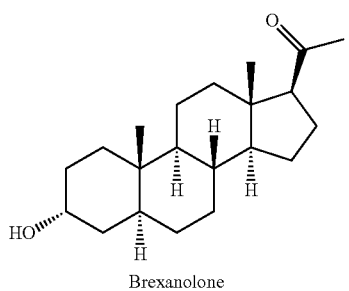

Brexanolone

State of the Art

Brexanolone was described for the first time in the patent GB 442,319 in 1934, assigned to Schering-Kahlbaum Aktiengesellschaft. The patent reports a brief experimental description of the preparation of the compound in question starting from 3-hydroxy-bisnorcholenic acid, which however has only a historical-academic value but no practical use.

A more recent synthesis process is described in the article "Synthesis of the allylic gonadal steroids, 3α-hydroxy-4-pregnen-20-one and 3α-hydroxy-4-androsten-17-one, and of 3α-hydroxy-5α-pregnan-20-one", J. P. Wiebe et al., Steroids (1985) Vol. 45, no. 1, pages 39-51. The synthesis is reported in the scheme in FIG. 1 on page 43 of the article; in this synthesis route, by causing 150 mg of compound 9 to react with potassium tri-s-butylborohydride (K selectride), 55 mg of brexanolone (compound 10 in the figure) are obtained after chromatographic purification.

The article "Synthesis, metabolism, and pharmacological activity of 3α-hydroxy steroids which potentiate GABA-receptor-mediated chloride ion uptake in rat cerebral cortical synaptoneurosomes", R. H. Purdy et al., Journal of Medicinal Chemistry, 1990, Vol. 33 (6), 1572-1581, describes another synthesis route of brexanolone, described with reference to scheme 1 on page 1573. In this synthesis a brexanolone sample (intermediate 2a) is obtained from the corresponding 3β isomer (intermediate 1) with a final yield of 54% after crystallisation and chromatographic purification (melting point=174-176° C.).

Patent EP 2 688 902 B1 describes a further synthesis of the compound. In this patent (example 5) a sample of brexanolone is obtained from the corresponding benzoate (intermediate 3, scheme 1 on page 8) with a final yield of 80% after chromatographic purification. The melting point, of 161.7-162.8° C., is however clearly lower than that described in the cited article by R. H. Purdy et al. This data, associated with the fact that the EP text does not contain information about purity, casts doubts on the quality of the product obtained. Upon experimental checks carried out by the present inventors, directed to evaluate the contents of the patent, it appears likely that the product obtained in this patent is brexanolone containing 16% of epimer in position 17, which has a melting range between 163.8<T<165.6° C. (DSC).

In the course of their experimental activities, the inventors have constantly observed the epimerisation of position 17 when brexanolone or one of its pregnane-structure synthesis intermediates with the unprotected carbonyl function are at acidic or basic pH, capable of generating an enolate intermediate or an enol in the course of the reaction.

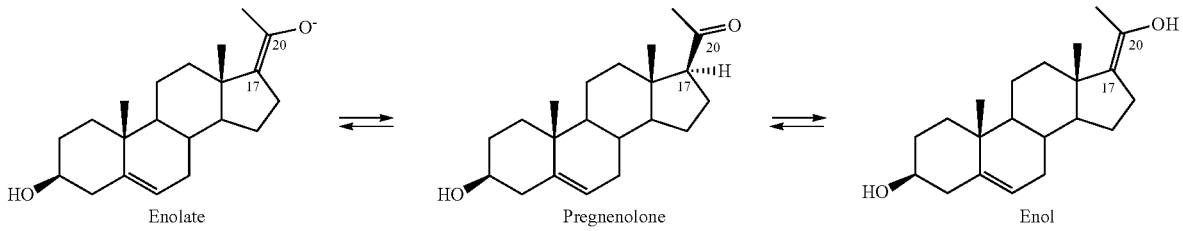 [SMILES: C/C([O-])=C1/CCC2C3CC=C4C[C@@H](O)CC[C@]4(C)C3CC[C@]12C ; CC(=O)[C@H]1CCC2C3CC=C4C[C@@H](O)CC[C@]4(C)C3CC[C@@]21C ; C/C(O)=C1/CCC2C3CC=C4C[C@@H](O)CC[C@]4(C)C3CC[C@]12C]

Enolate      Pregnenolone      Enol

The formation of the double bond generates an intermediate with a planar structure between the positions 17 and 20 that evolves in the reaction regenerating the single bond with spatial configuration both β, predominant, and α, minority but quantitatively relevant for the purpose of the quality required for a pharmaceutical product. Despite the research activity carried out by the present inventors, it has proved difficult, if not impossible, to identify the pH limits at which these unwanted reactions occur, since the reaction can take place in an organic solvent or aqueous organic solvent, at various concentrations and temperatures, and with different acids or bases.

In the course of their experimental activity the inventors also tried to protect the carbonyl in position 20 as a ketal with the use of ethylene glycol, but all the subsequent hydrolysis tests led to the epimerisation of position 17. The conditions tested for ketal deprotection were: HCl 1 M in methyl alcohol at 25° C.; para-toluenesulfonic acid (PTSA) 10 mol % in acetone at 55° C.; 5 mol % PTSA in acetone at 25° C.; 5 mol % PTSA in acetone at 0° C.; 1 mol % PTSA in acetone at 25° C.; pyridinium para-toluenesulfonate (PPTS) 5 mol % in acetone at 25° C.; anhydrous $FeCl_3$ in an acetone/dichloromethane mixture at 25° C.

Eliminating or at least limiting this unwanted chemical reaction (epimerisation) is relevant both for the process yield and for the quality of brexanolone.

The article "Improved syntheses of aromatase inhibitors and neuroactive steroids efficient oxidations and reductions at key positions for bioactivity", A. S. Campos Neves et al., Tetrahedron, 55 (1999) pages 3255-64 describes the epimerisation in position 17 on a steroid similar to brexanolone (scheme 1 on page 3257) in an acid environment; this undesired reaction involves the formation of 12% of by-product which is eliminated by crystallisation, with a yield of 60% reaching an intermediate with a purity of 95-97%, which however remains far from a pharmaceutical quality.

An object of the present invention is to provide a synthesis route for the preparation of brexanolone which is industrially applicable and which allows obtaining a product of pharmaceutical quality, overcoming the criticalities that associated to the described processes of the prior art.

SUMMARY OF THE INVENTION

This object is achieved with the present invention, which relates to a method for the preparation of brexanolone which consists in the deprotection of a cyclic ketal or a cyclic thioketal thereof of general formula (IV) with the use of iodine in an organic solvent, according to the reaction scheme:

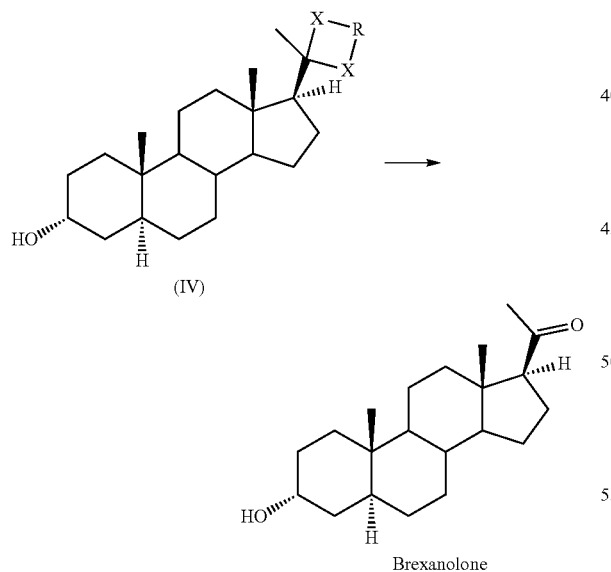

wherein is X=O (oxygen) in the case of ketal and X=S (sulfur) in the case of thioketal, and R is a radical selected among ethylene (—$CH_2$—$CH_2$—), propylene (—$CH_2$—$CH_2$—$CH_2$—) and 2,2-dimethylpropylene (—$CH_2$—C($CH_3$)$_2$—$CH_2$—).

The brexanolone obtained by means of this preparation method has an amount of epimer in position 17 lower than 0.15%, as determined by HPLC analysis.

In a preferred embodiment, the invention relates to a process for the synthesis of brexanolone comprising the following steps:

1) catalytic hydrogenation of the double bond in position 5,6 of pregnenolone in order to obtain the corresponding saturated steroid of formula (I), with the hydrogen atom in position 5 of the steroid skeleton in a spatial arrangement α:

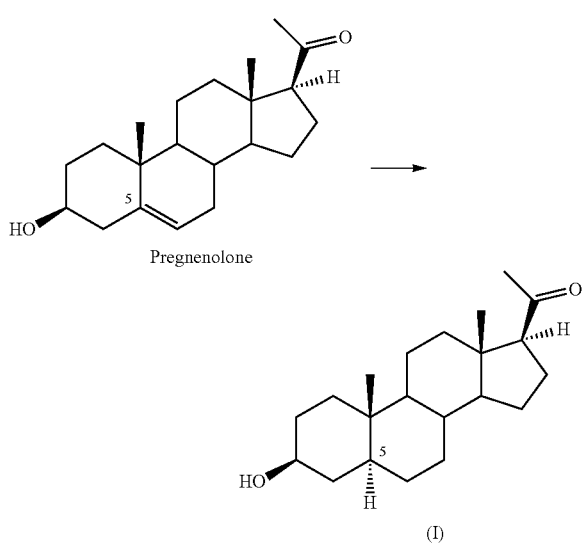

2) inversion of the spatial orientation of the hydroxyl in position 3 of the compound of formula (I) which, at the end of the reaction, is protected as benzoic ester, obtaining the compound of formula (II):

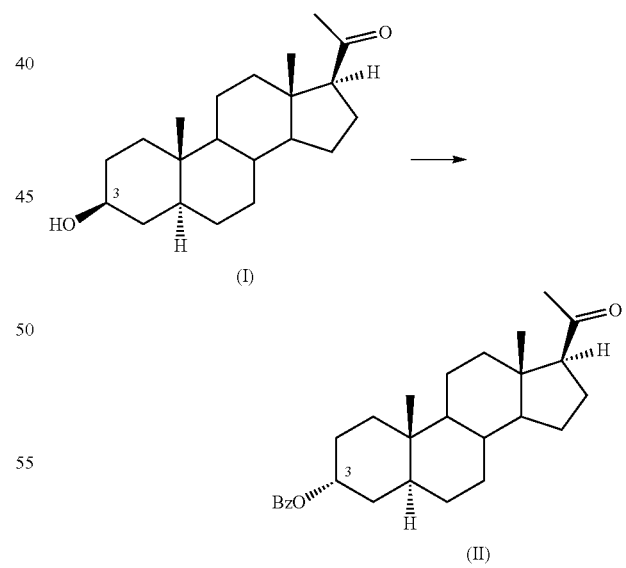

3) protection of the carbonyl in position 20 of the compound (II) as ketal or thioketal, obtaining the compound of general formula (III), wherein is X=O or X=S and R is a radical selected among ethylene (—$CH_2$—$CH_2$—), propylene (—$CH_2$—$CH_2$—$CH_2$—) and 2,2-dimethylpropylene (—$CH_2$—C($CH_3$)$_2$—$CH_2$—):

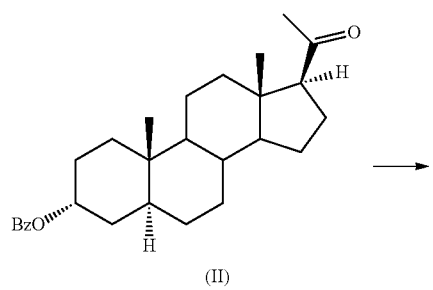
(II)
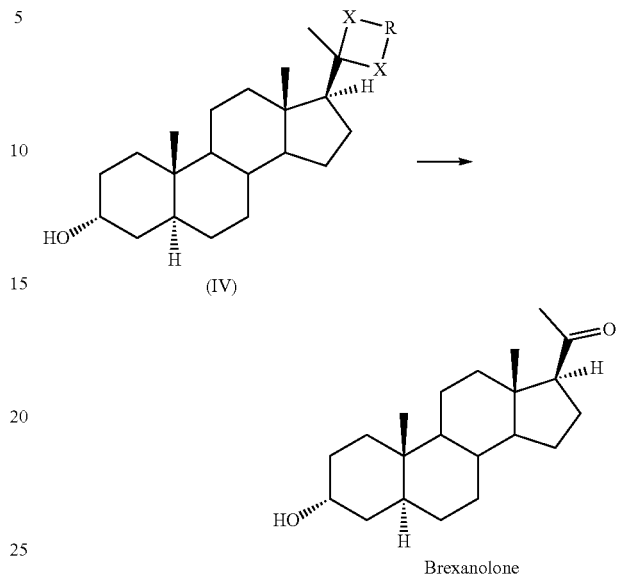
4) hydrolysis of the benzoic ester of the compound (III) obtaining the compound of general formula (IV), wherein X and R have the meanings reported above:
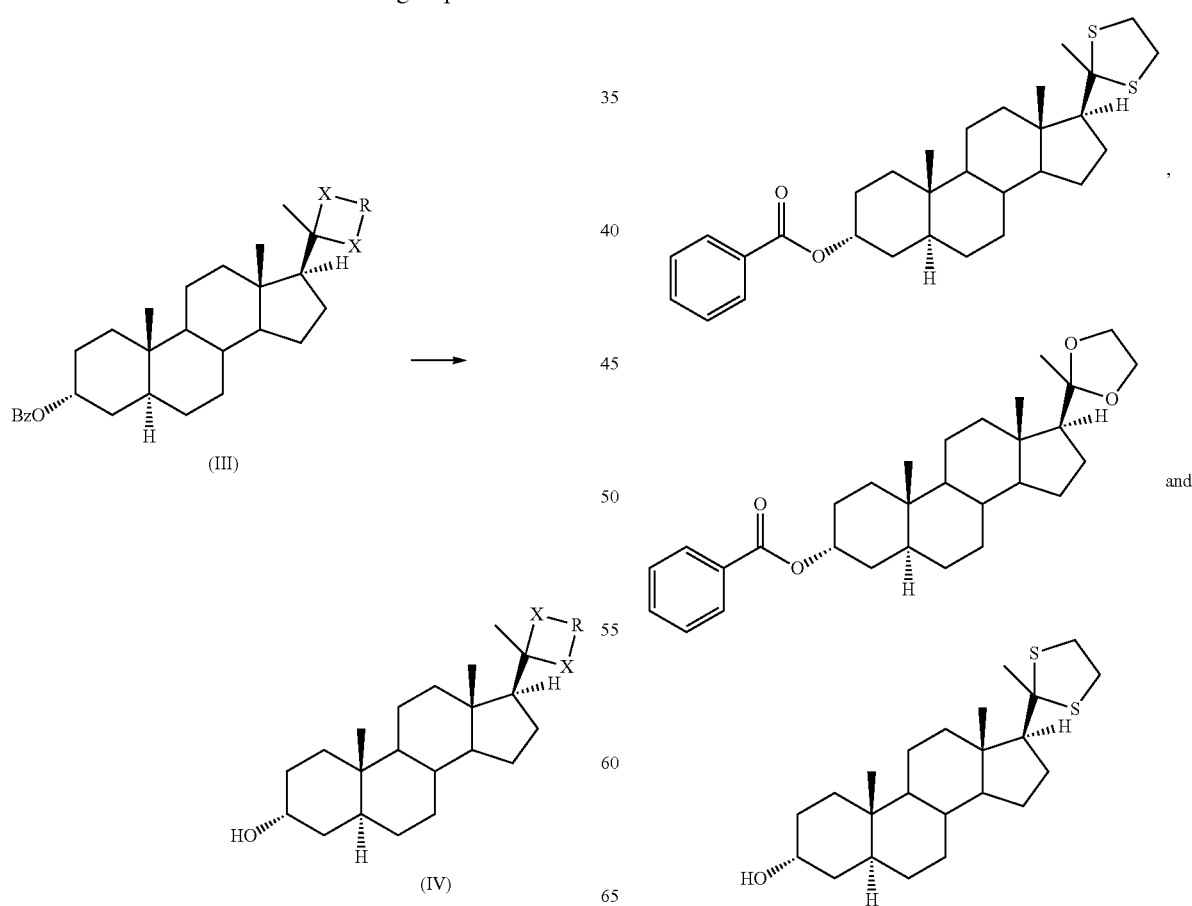
5) deprotection of the position 20 of the compound of general formula (IV) obtaining brexanolone:
In a second aspect thereof, the invention relates to the following intermediate synthesis compounds:

that is, the compounds of formula (III), wherein R is ethylene, both in the case X=S and in the case X=O, and the compound of formula (IV), wherein R is ethylene in the case X=S.

BRIEF DESCRIPTION OF THE DRAWINGS

FIG. 4: DSC thermogram of pure brexanolone obtained following the procedure of Example 5.

DETAILED DESCRIPTION OF THE INVENTION

Figure 1:
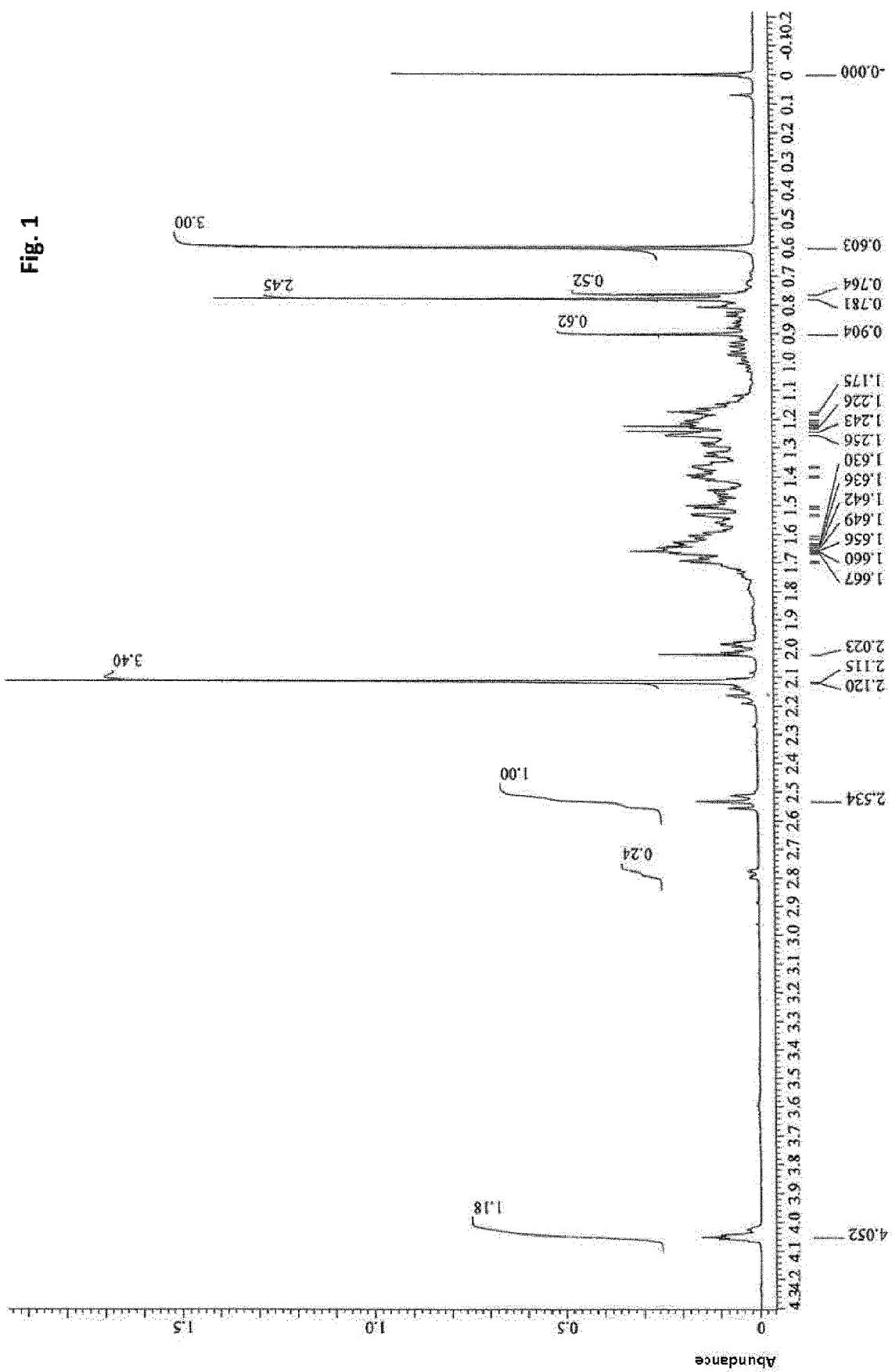
FIG. 1: NMR spectrum of the brexanolone-epimer mixture obtained in the preparation described in Example 6.

In the present description and in the claims, in case of a discrepancy between the name of a compound and the structure formula reported for it, the latter must be considered correct.

The object of the present invention, in its first aspect, is a method for the preparation of brexanolone which consists in the deprotection of a cyclic ketal or a cyclic thioketal thereof of general formula (IV) with the use of iodine in an organic solvent, according to the reaction scheme:

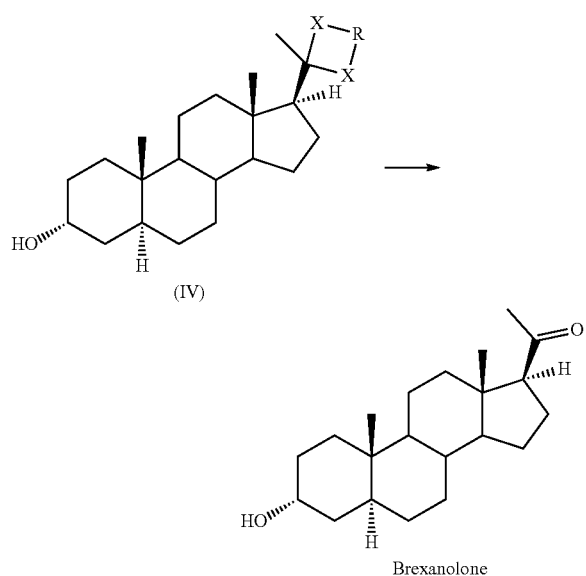

wherein is X=O (oxygen) in the case of ketal and X=S (sulfur) in the case of thioketal, and R is a radical selected among ethylene (—CH$_2$—CH$_2$—), propylene (—CH$_2$—CH$_2$—CH$_2$—) and 2,2-dimethylpropylene (—CH$_2$—C(CH$_3$)$_2$—CH$_2$—).

In the preferred embodiment of the invention R is the ethylene radical, —CH$_2$—CH$_2$—.

The conditions of the reaction are different depending on whether the compound of formula (IV) is a ketal or a thioketal.

In the case X=O, the ketal must be hydrolysed in a neutral environment, avoiding the presence of acids or bases. Preferably, for the deprotection of the ketal, iodine is used in an amount between 1 and 10% by weight with respect to the amount of compound (IV).

As the reaction solvent it is possible to use anhydrous acetone or a mixture of dichloromethane and acetone operating in the absence of water. Operating with anhydrous acetone or with a mixture of dichloromethane and acetone in the absence of water is decisive for the outcome of the reaction.

The reaction temperature is between −5° C. and the reflux temperature of the reaction mixture.

The reaction time is between 5 and 90 minutes. Preferably one operates in the range between 10 and 45 minutes.

In the case X=S, the thioketal is reacted with iodine in organic solvent at a temperature between −30 and 20° C. in the presence of a solid inorganic base such as sodium carbonate, lithium carbonate, potassium carbonate, calcium carbonate, sodium bicarbonate, lithium bicarbonate and potassium bicarbonate; the preferred base is sodium bicarbonate. As the organic solvent, dichloromethane (DCM), methanol or, preferably, a mixture thereof, can be used.

The reaction time is between 2 and 36 hours and is related to the amount of iodine used in the reaction and to the reaction temperature. Preferably one operates in the temperature range between −25 and −5° C. for a period of time between 1 and 18 hours.

The inventors have experimentally observed that by means of this synthesis process it is possible to obtain brexanolone which has an amount of epimer in position 17 lower than 0.15% (value determined by HPLC analysis), a value which corresponds to the maximum amount admitted by the ICH guidelines issued by the European Medicines Agency (EMA) for the identified impurities present in active ingredients and intermediate products for the pharmaceutical industry (API) for which no pharmacological studies have been carried out that allow the presence thereof in a higher amount. This result is possible by operating under the conditions of the invention without resorting to chromatographic purifications or to special purification techniques to be applied to the produced brexanolone.

In particular, the brexanolone obtained according to the method of the invention, in the case X=S, is substantially free of its epimer in position 17 and therefore no specific purification treatment is required to eliminate this impurity. In the case X=O in the raw product the presence of a minimum amount of epimer in position 17, lower than 0.5%, is observed, which is easily reduced to values lower than 0.1% by crystallisation.

In a preferred embodiment, the invention relates to a complete process for the industrial-scale synthesis of brexanolone comprising the steps 1 to 5 reported above.

The reactions of steps 1) from pregnenolone to compound of formula (I), 2) from compound of formula (I) to compound of formula (II), and 4) from compound of general formula (III) to compound of general formula (IV), are executable following the indications available in the literature, such as those reported in patent EP 2 688 902 B1; these steps are therefore summarily described below.

In step 1) the intermediate (I) is produced starting from pregnenolone:

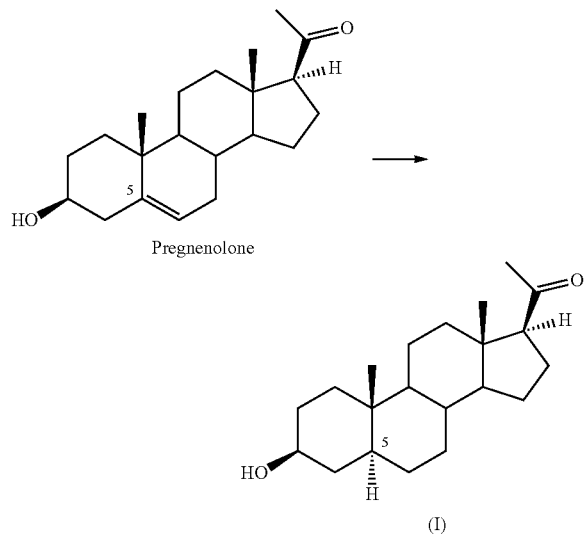

Starting pregnenolone is a commercially available compound. The methods of execution of this step are known in the art.

For the purposes of the present invention, preferred conditions are the use of palladium supported on carbon (Pd/C) at 5% as a hydrogenation catalyst. The amount used is about 5% of the weight of pregnenolone to be hydrogenated. The hydrogenation pressure is between 2 and 5 bar. The reaction solvent is tetrahydrofuran (THF). The hydrogenation temperature is between 35 and 45° C. The hydrogenation time is variable between 3 and 7 hours, the reaction is over when the consumption of hydrogen ceases.

In step 2) it is brought about the inversion of the spatial orientation of the hydroxyl in position 3 of intermediate (I) which, at the end of the reaction, is protected as a benzoic ester (intermediate (II)):

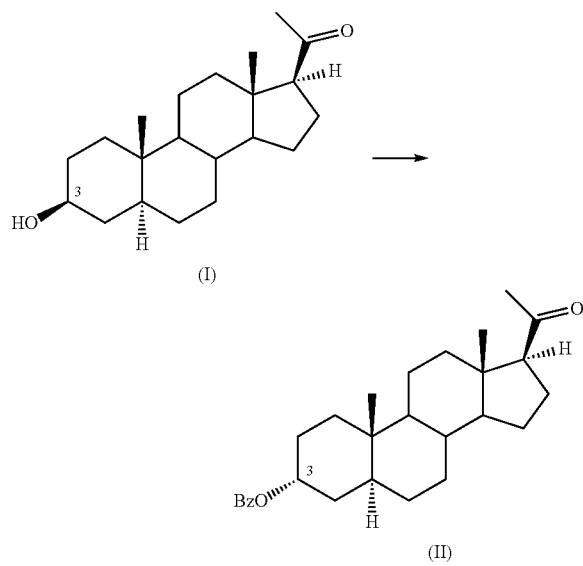

Also this step is executable according to methods known in the field.

In the case of the present invention this step is preferably carried out by preparing the benzoic ester of the hydroxyl in position 3, causing the intermediate (I) to react with benzoic acid in tetrahydrofuran (THF) as the solvent and allowing the system to react for 14-20 hours with triphenylphosphine and diisopropyl azodicarboxylate (DIAD) at 15-25° C.

The intermediate (II) thus obtained is then purified by refluxing it in an alcohol, preferably methanol, obtaining a quality suitable for continuing the synthesis.

In step 3) the carbonyl in position 20 of the intermediate (II) is protected as ketal or thioketal, obtaining the intermediate of general formula (III), wherein is X=O or X=S and R is a radical selected from ethylene (—$CH_2$—$CH_2$—), propylene (—$CH_2$—$CH_2$—$CH_2$—) and 2,2-dimethylpropylene (—$CH_2$—$C(CH_3)_2$—$CH_2$—):

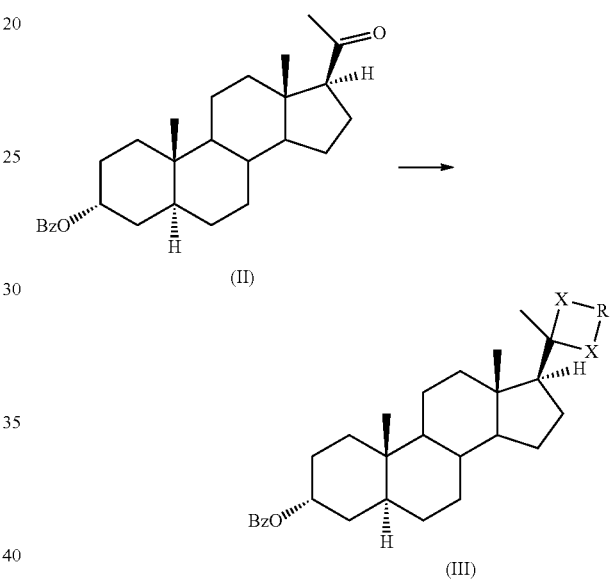

The ketal (X=O) can be obtained bringing under reflux a mixture of intermediate (II) with toluene, ethylene glycol, propylene glycol or 2,2-dimethylpropylene glycol, triethylorthoformate and p-toluenesulfonic acid. In this case, an amount between 5 and 10% of epimer 17a is formed, which is eliminated by crystallizing the raw intermediate (III) with an organic solvent, such as for example ethyl acetate, isopropyl acetate or 2-propanol.

The obtention of the thioketal is possible by causing the intermediate (II) to react with propanedithiol, 2,2-dimethylpropanedithiol or, preferably, etanedithiol in a solvent selected among acetic acid, dichloromethane ($CH_2Cl_2$), ethyl ether, acetonitrile, tetrahydrofuran (THF) and 1,2-dichloroethane, in the presence of a catalyst selected among boron trifluoride etherate ($BF_3 \cdot Et_2O$), zinc iodide ($ZnI_2$), titanium tetrachloride ($TiCl_4$), tin dichloride ($SnCl_2$), magnesium iodide ($MgI_2$), lithium perchlorate ($LiClO_4$), aluminium trifluoromethanesulfonate (also known as aluminium triflate, $Al(OTf)_3$), lithium tetrafluoroborate ($LiBF_4$) and cobalt dichloride ($CoCl_2$), at a temperature in the range between 15 and 45° C. and for a time between 8 and 36 hours. The preferred reaction conditions envisage the use of acetic acid as the solvent, of etherate $BF_3$ ($BF_3 \cdot Et_2O$) as catalyst at a temperature of 30±5° C. for a period of 24-28 hours.

In step 4) the hydrolysis of the benzoic ester of the intermediate of general formula (III) is carried out, obtaining the intermediate of general formula (IV):

(III)

(IV)

This step is executable following the indications available in the prior art.

In the case of the present invention this step is preferably carried out by refluxing the intermediate (III) in methanol for a period of 20-28 h in the presence of a strong base such as sodium hydroxide, and monitoring the progress of the reaction, for example with TLC.

Finally, step 5) of the process corresponds to the method of deprotection of ketals or thioketals according to the first aspect of the invention, described in detail above.

The invention will be further illustrated by the following examples.

Instruments, Methods and Experimental Conditions

NMR:
NMR spectrometer JEOL 400 YH (400 MHz); JEOL Delta software v5.1.1;
Spectra recorded in deuterated solvents: Chloroform-d, D 99.8%, containing 0.1% (v/v) tetramethylsilane (TMS) as internal standard; Chloroform-d, "100%", D 99.96%, containing 0.03% (v/v) TMS; $CD_3OD$; and DMSO-d6.

MS
Instrument: DSQ-trace Thermofisher;
Sample introduction—direct exposure probe (dep);
Chemical ionisation (CI) methane;
Source temperature: 200° C.

DSC
Instrument Perkin Elmer mod. Diamond;
Perkin Elmer Standard Aluminium capsules and lids, code 02190041;
Scan speed: 10° C./min;
Temperature range: from 20° C. to 220° C.

HPLC
For Pregnenolone, Intermediate (I), and Brexanolone
Agilent chromatographic system model 1260 Infinity; UV detector MODEL 1260 DAD VL; Column Advanced Chromatography Technologies ACE 3 C18-PFP 150×3 mm, 3 μm; mobile phase A: water, mobile phase B: acetonitrile, isocratic method 50/50, wavelength 200 nm, flow rate 0.5 ml/min, injection volume 5 μl, run time 25 min, temperature 25° C.;

For the intermediates (II), (III) and (IV)
Agilent chromatographic system model 1260 Infinity; UV detector MODEL 1260 DAD VL; Column: Supelco Ascentis C8 150×4.6 mm, 5 μm; mobile phase A: water, mobile phase B: methanol; 85/15 isocratic method, wavelength 216 nm, flow rate 1 ml/min, injection volume 5 μl, run time 45 min, temperature 25° C.

LC/Ms/Ms System
Agilent chromatographic system model 1100 with UV DAD detector connected to an API 2000 mass spectrometer by Applied Biosystem.

TLC
MERCK: TLC silica gel 60 $F_{254}$ Aluminium sheets 20×20 cm, code 1.0554.0001.

HPTLC
MERCK: HPTLC silica gel 60 $F_{254}$ with concentration zone 10×2.5 cm, code 1.13727.0001.

TLC Detectors
Acid solution of cerium phosphomolybdate. Preparation: 25 g of phosphomolibdic acid hydrate (Aldrich), 10 g cerium (IV) sulphate hydrate (Aldrich) and 600 ml of water are stirred until dissolution with 60 ml of sulfuric acid 95-98% (Aldrich 258105); it is brought to a final volume of 1000 ml with water; the sheet is impregnated with a solution then heated until blue colouration.

TLC and HPTLC Eluent
The conditions of the TLC checks are reported in the experimental procedures.

Specifications Regarding the Experimental Descriptions of the Examples:

The water used in the experimental descriptions is to be understood as pure water unless otherwise indicated.

The organic solvents used in the experimental descriptions are to be understood as of "technical" grade unless otherwise indicated.

The reagents and catalysts used in the experimental descriptions are to be understood of commercial quality unless otherwise indicated.

Example 1

This example relates to step 1) of the process of the invention.

Pregnenolone

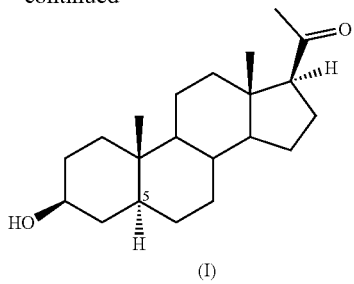

(I)

10 g of pregnenolone were dissolved in 300 ml of THF at 20±5° C. and the solution was loaded into a hydrogenation reactor. 0.50 g of Pd/C at 5% were added. Two vacuum/hydrogen cycles were performed and finally hydrogen was loaded up to a pressure of 4 bar.

The reagent mixture was heated to 40±5° C., maintaining under stirring until the end of hydrogen consumption was observed (about 5 hours). A $^1$H-NMR check was made noting the complete disappearance of the starting pregnenolone.

The reagent mixture was cooled to 20±5° C. and filtered on celite, washing with 50 ml of THF. THF was eliminated with rotavapor, heating up to 40-45° C. Methyl ethyl ketone (MEK, 50 ml) was loaded and the mixture was distilled with rotavapor, heating up to 45° C. twice. 30 ml of MEK were loaded and the mixture was stirred under reflux for 10 minutes (no dissolution was noted). The mixture was cooled down to 0° C. and maintained under stirring for 1 h, after which it was filtered and washed with cold MEK. The solid was dried in an oven at 40° C. for 4 h, obtaining 9.2 g of white solid (intermediate (I)).

Pregnenolone Analysis:

$^1$H-NMR, CDCl$_3$: 5.36-5.35 (1H, m, H-6); 3.57-3.49 (1H, m, H-3); 2.54 (1H, t, J=9 Hz, H-17); 2.34-2.15 (2H, m); 2.13 (3H, s, H-21); 2.07-1.97 (2H, m); 1.89-1.82 (2H, m); 1.73-1.41 (10H, m); 1.29-1.06 (3H, m); 1.01 (3H, s, CH$_3$); 0.63 (3H, s, CH$_3$);

Mass: 316 (M$^+$).

Analysis of Intermediate (I):

$^1$H-NMR, CDCl$_3$: 3.64-3.56 (1H, m, H-3); 2.52 (1H, t, J=9 Hz, H-17); 2.2-2.1 (1H, m); 2.11 (3H, s, H-21); 2.00 (1H, dt, J=3-11.4 Hz); 1.84-1.53 (8H, m); 1.50-0.84 (11H, m); 0.80 (3H, s, CH$_3$); 0.68 (1H, dt, J=4-12 Hz); 0.60 (3H, s, CH$_3$);

Mass: 318 (M$^+$).

Example 2

This example relates to step 2) of the process of the invention.

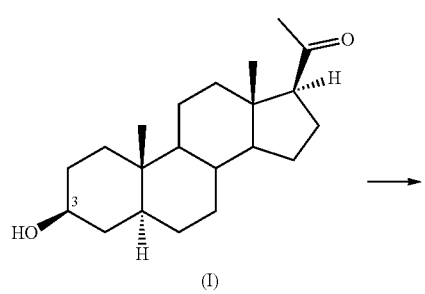

(I)

15.8 g of intermediate (I) obtained in the previous example were loaded into a flask under a nitrogen atmosphere at 20-25° C. 390 ml of THF were added and the mixture was stirred until dissolution. 9.1 g of benzoic acid and 19.4 g of triphenylphosphine were added. In the reaction mixture 15.3 ml of 94% DIAD were dripped over 30 minutes, maintaining the temperature below 30° C. The mixture was stirred at 20±5° C. for 16 hours and a TLC check was performed, observing the complete disappearance of the starting reagent. The TLC check was carried out under the following conditions:

start: in CH$_2$Cl$_2$;

sample: reaction mix in ethyl acetate. The organic phase is deposited;

eluent: toluene/isopropyl acetate 8/2; sheet: HPTLC glass;

detector: UV/phosphomolybdic cerium.

THF was distilled in the rotavapor under vacuum at 45±5° C. The obtained residue was dissolved with 250 ml of ethyl acetate at 20±5° C. and 200 ml of aqueous solution saturated with NaHCO$_3$ were added. Stirring was maintained for 10 minutes at 20±5° C., then the phases were separated. The organic phase was washed with 200 ml of aqueous solution saturated with NaHCO$_3$ and the phases were separated. The aqueous phases were reunited and re-extracted with ethyl acetate. The organic phases were reunited and washed with 130 ml of aqueous solution saturated with NaCl. The phases were separated and the organic phase was washed with 100 ml of water. The phases were separated and the organic phase was distilled with rotavapor at reduced pressure at 45±5° C. 150 ml of heptane were added and the mixture distilled with rotavapor at reduced pressure at 40±5° C. until all the solvent was eliminated and then for another 30 minutes. 62.0 g of an almost white solid were obtained. The solid was suspended in 120 ml of MeOH at 20±5° C., and the suspension heated under reflux for 10 minutes; total dissolution was not observed. The system was allowed to cool spontaneously down to 20±5° C. and then with an ice bath down to 0±5° C., maintaining it under stirring at this temperature for 1 hour. The mixture was filtered on büchner funnel by washing with 40 ml of MeOH pre-cooled at 0±5° C. The solid was vacuum dried in an oven at 45±5° C. for 16 hours, obtaining 19.7 g of white solid (intermediate (II)).

Analysis of Intermediate (II):

$^1$H-NMR, CDCl$_3$: 8.07 (2H, dd, J=1.5-8.6 Hz, aromatic H); 7.59-7.53 (1H, m, aromatic H); 7.46 (2H, t, J=7.8 Hz, aromatic H); 5.29 (1H, m, H-3); 2.54 (1H, t, J=9 Hz, H-17); 2.20-0.80 (22H, m); 2.12 (3H, s, H-21); 0.85 (3H, s, CH$_3$); 0.62 (3H, s, CH$_3$);

Mass: 423 (M$^+$+1).

Example 3

This example relates to step 3) of the process of the invention, in the case X═S and R=ethylene, —CH$_2$—CH$_2$—.

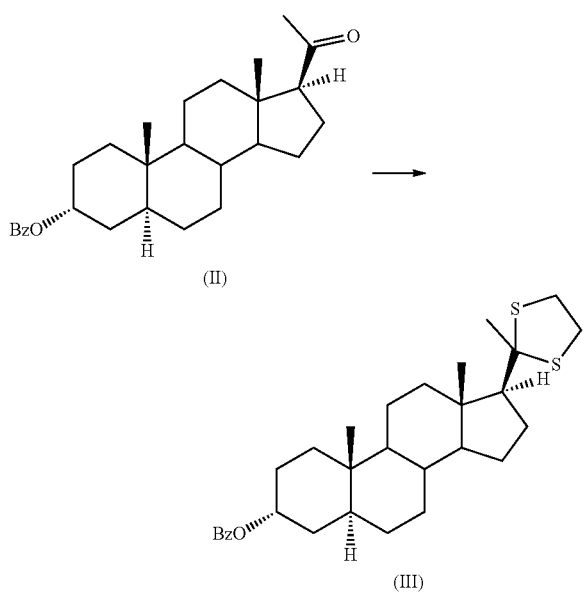

(II)

(III)

In a reaction flask under nitrogen, 17 g of intermediate (II) obtained in the previous example and subsequently 85 ml of glacial acetic acid were loaded: no complete dissolution was noted. 3.7 ml of 1,2 ethanitiol were added. On the reaction mixture 3.7 ml of boron trifluoride-ethyl ether complex ($BF_3 \cdot Et_2O$) were dripped over about 10 minutes, without exceeding 25° C. The system was maintained under stirring at 30±5° C. for a total of 26 h by adding portionwise further 3.8 ml of ethanitiol and checking the progress of the reaction by TLC (constant intermediate (II) spot). The TLC check was carried out under the following conditions:

start: in THF;
sample: NaOH 10%+toluene;
eluent: heptane/isopropyl acetate 8:2; sheet: silica gel;
detector: UV/phosphomolybdic cerium.

Upon completion of the reaction, the mixture was cooled to 20° C. A 10 wt/% NaOH solution cooled to 0° C. was separately prepared by diluting 226 g of a 30 wt/% NaOH solution with 452 g of water. The reaction mixture was poured onto the cold soda solution without exceeding 10° C. (the formation of a precipitate was observed). The reaction flask was washed with water (150 ml), which was added to the basic mixture containing the product. The suspension thus obtained was stirred for 1 h at a temperature≤20° C. The solid was filtered on bûchner funnel and washed with water (500 ml) until neutral pH was reached. The solid on the filter was dissolved with dichloromethane (400 ml), washed with 1.5% sodium hypochlorite solution and then with water. The solvent was eliminated by evaporation at reduced pressure at 45° C., obtaining 22.6 g of yellow solid (raw intermediate (III)). 20 g of this intermediate were loaded into a flask under nitrogen. 60 ml of MEK were added and the mixture was heated under reflux (no complete dissolution was observed). The system was allowed to cool spontaneously to 25° C. and then cooled to 0° C. for 1 hour. The mixture was filtered on bûchner funnel and the solid washed with cold MEK. The solid was dried at 45° C. at reduced pressure for 2 hours obtaining 10.3 g of white solid (intermediate (III)).

Analysis of Intermediate (III):

$^1$H-NMR, $CDCl_3$: 8.07 (2H, dd, J=1.4-8 Hz, aromatic H); 7.56 (1H, dt, J=1.4-7.3 aromatic H); 7.46 (2H, t, J=7.5 Hz, aromatic H); 5.30-5.28 (1H, m, H-3); 3.40-3.13 (4H, m, $SCH_2CH_2S$); 2.12-0.89 (23H, m); 1.87 (3H, s, H-21); 0.84 (3H, s, $CH_3$); 0.81 (3H, s, $CH_3$);

$^{13}$C-NMR, $CDCl_3$: 165.92 (C=O); 132.70 (aromatic CH); 131.14 (aromatic C); 129.53 (2 aromatic CH); 128.32 (2 aromatic CH); 71.41 (C, S—C—S); 70.70 (CH, C-3); 60.76 (CH); 56.41 (CH); 54.14 (CH); 44.27 (C); 41.41 ($CH_2$); 40.39 (CH); 40.06 ($CH_2$); 37.29 ($CH_2$); 35.86 (C); 35.61 ($CH_3$, C-21); 35.10 (CH); 33.17 ($CH_2$); 32.97 ($CH_2$); 31.74 ($CH_2$); 28.32 ($CH_2$); 26.98 ($CH_2$); 26.29 ($CH_2$); 23.94 ($CH_2$); 20.73 ($CH_2$); 13.36 ($CH_3$); 11.41 ($CH_3$);

Mass: 498 ($M^+$).

Example 4

This example relates to step 4) of the process of the invention, in the case X=S and R=ethylene, —$CH_2$—$CH_2$—.

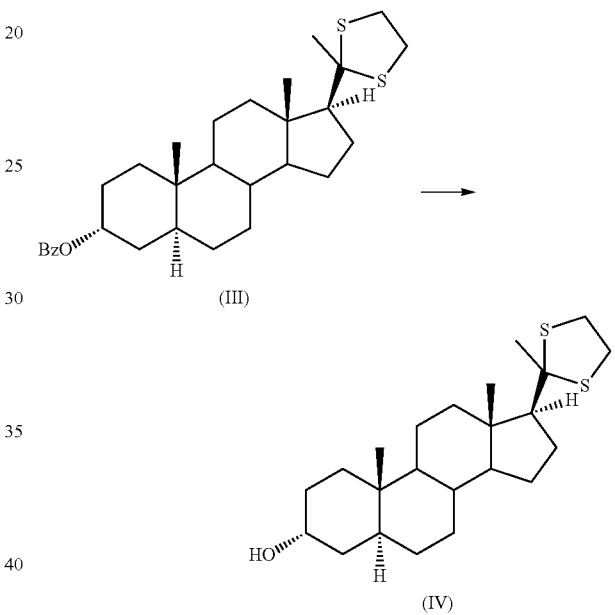

(III)

(IV)

10.1 g of intermediate (III) obtained in the previous example were loaded into a flask under a nitrogen flow. 250 ml of methanol were added; no complete dissolution was noted. 20.3 g of NaOH were added and the mixture was heated under reflux for 25 hours maintaining it under stirring. A TLC check was carried out, observing the completion of the reaction. The TLC check was carried out under the following conditions:

start: in dichloromethane;
reaction: in dichloromethane;
eluent: Eptane/isopropyl acetate 8:2; sheet: silica gel;
detector: UV/phosphomolybdic cerium.

The reaction mixture was cooled to 25° C. and 300 ml of water were added. Methanol was distilled at reduced pressure with rotavapor. The formation of a precipitate was observed, 350 ml of dichloromethane were added and the system was maintained under stirring for 10 minutes at 35° C., noting the complete dissolution of the solid. The phases were separated and the aqueous phase re-extracted with 100 ml of dichloromethane at 35° C. The organic phases were reunited and washed with water (3 times×300 ml) until neutral pH was reached. The solvent was eliminated by evaporation at reduced pressure obtaining 8.3 g of white solid (intermediate (IV)).

Analysis of Intermediate (IV):

$^1$H-NMR, CDCl$_3$: 4.04 (1H, m, H-3); 3.4-3.1 (4H, m, SCH$_2$CH$_2$S); 2.11-0.86 (23H, m); 1.86 (3H, s, H-21); 0.80 (3H, s, CH$_3$); 0.78 (3H, s, CH$_3$);

$^{13}$C-NMR, CDCl$_3$: 71.43 (C, S—C—S); 66.58 (CH, C-3); 60.70 (CH); 56.43 (CH); 54.11 (CH); 44.25 (C); 41.39 (SCH$_2$); 40.08 (CH$_2$); 39.07 (CH); 37.29 (SCH$_2$); 36.04 (C); 35.84 (CH$_2$); 35.58 (CH$_3$, C-21); 35.12 (CH); 32.12 (CH$_2$); 31.81 (CH$_2$); 28.98 (CH$_2$); 28.48 (CH$_2$); 26.97 (CH$_2$); 23.93 (CH$_2$); 20.66 (CH$_2$); 13.35 (CH$_3$); 11.18 (CH$_3$);

Mass: 394 (M$^+$).

Example 5

This example relates to step 5) of the process of the invention starting from a thioketal.

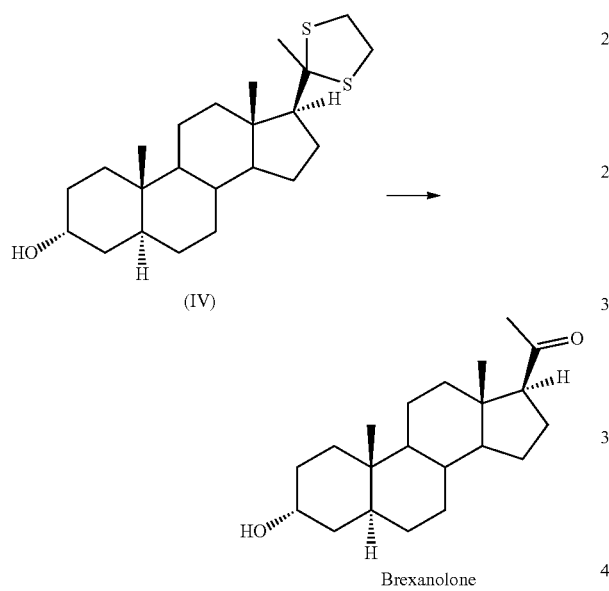

8 g of intermediate (IV) obtained in the previous example were loaded into a flask under nitrogen. Dichloromethane (56 ml) and methanol (88 ml) were added; no complete dissolution was observed. The system was cooled to −20° C. and NaHCO$_3$ (15.3 g) was added. I$_2$ (15.5 g) was added and the system was maintained under stirring at −20° C. for 4 h, adding NaHCO$_3$ (4.95 g) and I$_2$ (5.15 g) in portions, and checking the progress of the reaction by TLC (complete reaction). The TLC check was carried out under the following conditions:

start: in THF;
reaction: in aqueous solution of Na$_2$S$_2$O$_3$, extracted with dichloromethane, the organic phase is seeded;
eluent: heptane/isopropyl acetate 1:1; sheet: silica gel;
detector: UV/phosphomolybdic cerium.

The reaction was quenched by dripping on the reaction mixture a solution of Na$_2$S$_2$O$_3$.5H$_2$O (45.3 g) in water (90 ml) maintaining the temperature below −15° C. (exothermic was noted, but no problems of freezing of the present water were observed). The system was brought to 20° C. and the suspension was filtered on a dicalite panel, washing the solid on the filter with dichloromethane preheated to 35° C. The phases were separated, the aqueous phase was extracted with dichloromethane; the organic phases were reunited and washed with water.

The solvent was eliminated by evaporation at reduced pressure with rotavapor obtaining 6.2 g of yellow powder (raw brexanolone) which were checked in HPLC; the HPLC chromatogram of raw brexanolone thus obtained shows that the epimer content is not detectable.

4.5 g of raw brexanolone were purified with a chromatographic column (120 g silica gel) eluting with dichloromethane first and then with acetone obtaining 4.1 g of product which is crystallized with dichloromethane/methyl-t-butyl ether, obtaining 3.9 g of pure brexanolone. FIG. 4 shows the thermogram obtained with the product with DSC technique (sample of 1.158 mg; test conditions indicated above); for clarity of representation only the part of the thermogram above 120° C. is shown. The figure shows that the sample melts between 174 and 176° C., which is the melting range for the pure product reported in the article by R. H. Purdy et al. mentioned above.

Brexanolone Analysis:

$^1$H-NMR, CDCl$_3$: 4.05 (1H, m, H-3); 2.53 (1H, t, J=9 Hz, H-17); 2.20-2.10 (1H, m); 2.11 (3H, s, H-21); 2.00 (1H, dt, J=3.2-11.9 Hz); 1.85-0.75 (20H, m); 0.78 (3H, s, CH$_3$); 0.60 (3H, s, CH$_3$);

Mass: 318 (M$^+$).

Example 6

This example relates to the epimerisation of brexanolone in a basic environment.

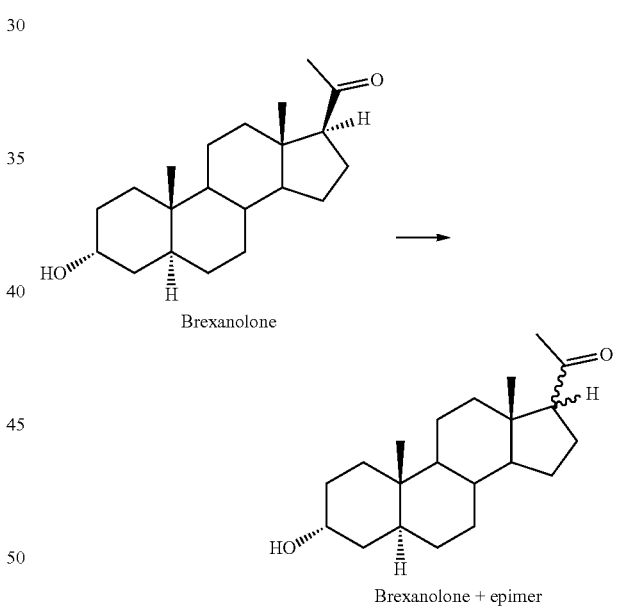

50 mg of brexanolone obtained following the preparation of Example 5 were dissolved in 1.25 ml of methanol and brought under reflux for 16 h with 38 mg of NaOH. The reaction mixture was cooled, methanol was evaporated under reduced pressure, the solid was taken up with water and dichloromethane, the phases were separated and the organic phase was washed until neutral pH was reached. The dichloromethane was evaporated obtaining a raw product which was purified by chromatographic column (heptane/isopropyl acetate 6:4), obtaining 22 mg of product. By NMR analysis the content of epimer 17a was determined on the basis of the ratio of signals of the proton in position 17.

FIG. 1 shows the expansion from 0 to 4.3 ppm of the NMR spectrum; the proton signals in position 17, on the basis of which the amount of brexanolone and epimer was calculated, are at 2.53 and 2.79 ppm. The epimer content was 19%.

The epimerisation was tested under similar conditions also on the intermediate (I) obtaining comparable results in terms of epimer formation.

H-NMR, CDCl$_3$: 4.05 (1H, m, H-3); 4.03 (1H, m, H-3 isomer 17a); 2.79 (dd, J=2.7-8.2 Hz, H-17 isomer 17a); 2.53 (1H, t, J=9 Hz, H-17); 2.120 (s, H-21 isomer 17a); 2.115 (3H, s, H-21); 0.904 (s, CH$_3$ isomer 17a); 0.781 (3H, s, CH$_3$); 0.764 (s, CH$_3$ isomer 17a); 0.603 (3H, s, CH$_3$).

Example 7

This example relates to the epimerisation of brexanolone in an acid environment. 50 mg of brexanolone obtained following the preparation of Example 5 were dissolved in 1.2 ml of THF to which 0.5 ml of HCl 2 M were added, heating the mixture under reflux for 16 h. The reaction mixture was cooled, THF was evaporated under vacuum, the solid was taken up with water and dichloromethane, the phases were separated and the organic phase was washed until neutral pH was reached. The dichloromethane was evaporated at reduced pressure, obtaining 42 mg of white solid.

Figure 2:
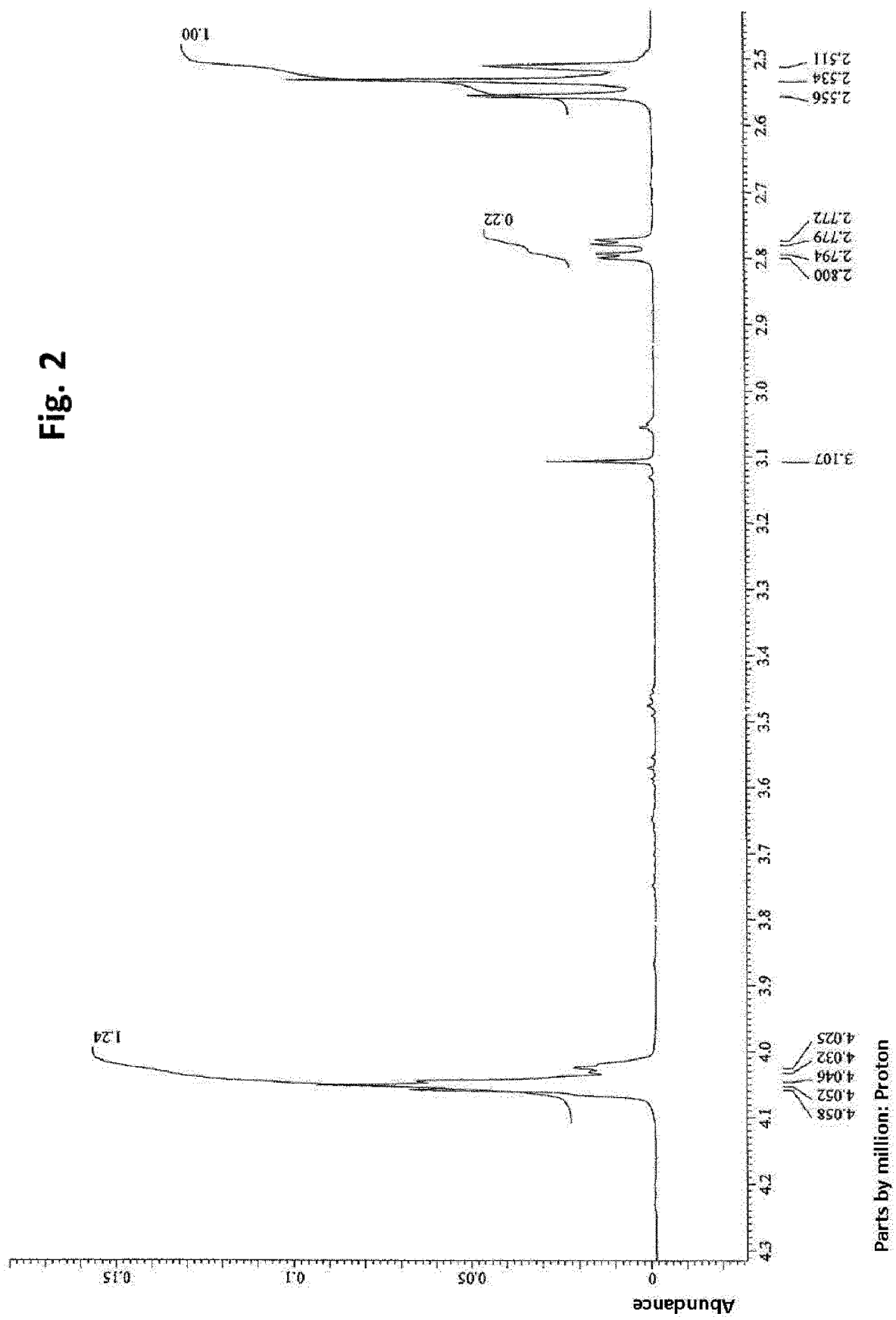
FIG. 2: NMR spectrum of the brexanolone-epimer mixture obtained in the preparation described in Example 7.
Figure 3:
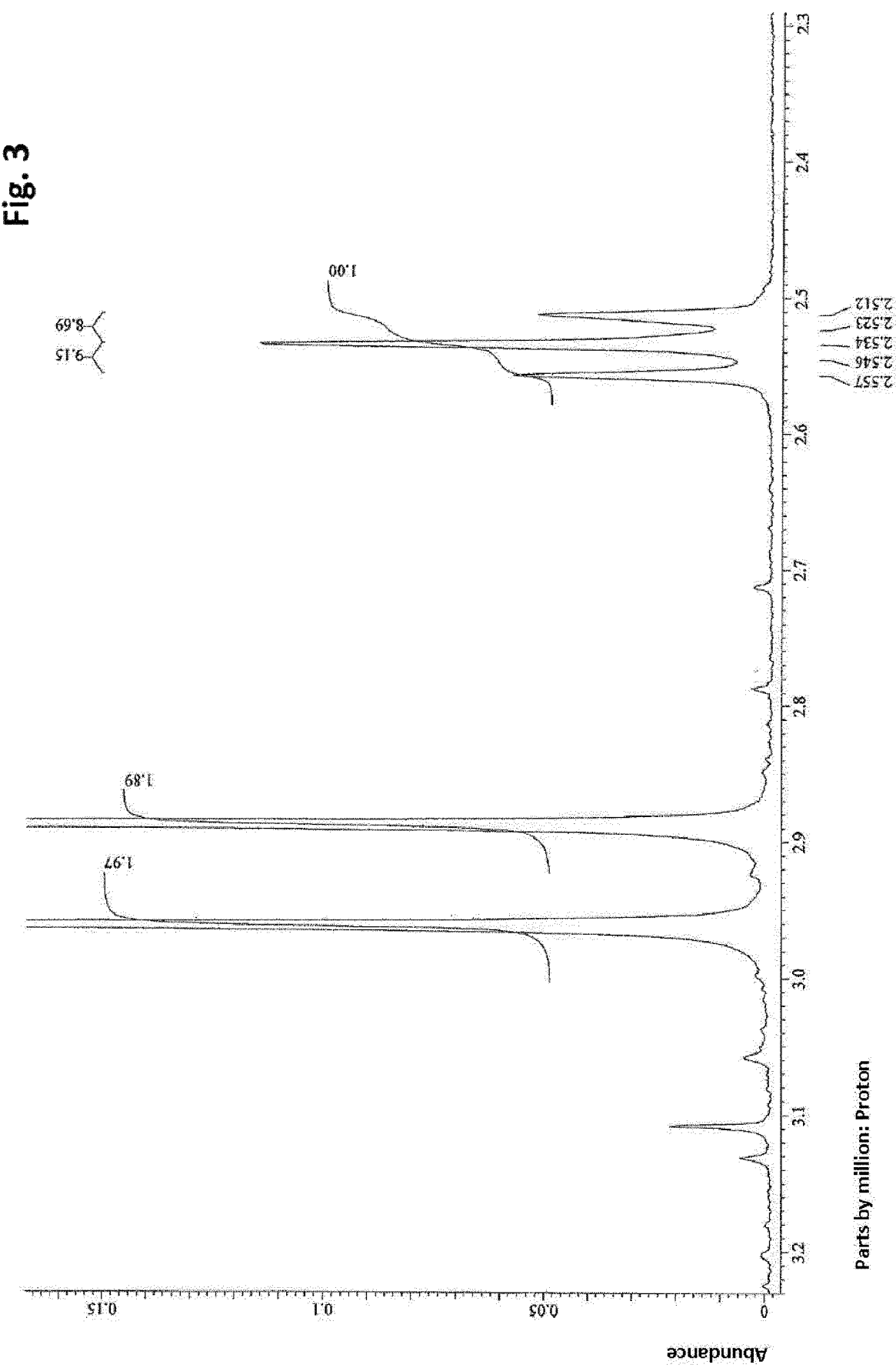
FIG. 3: NMR spectrum of epimer-free brexanolone. The expansion from 2.3 to 3.2 ppm is reported.

FIG. 2 shows the expansion from 2.5 to 4.3 ppm of the NMR spectrum; the signals relating to brexanolone and epimer are the same indicated in Example 6 with reference to FIG. 1. The ratio of the signals shows that the product had a 17a epimer content of 18%.

Example 8

This example relates to step 3) of the process of the invention, in the case X=O and R=ethylene, —CH$_2$—CH$_2$—.

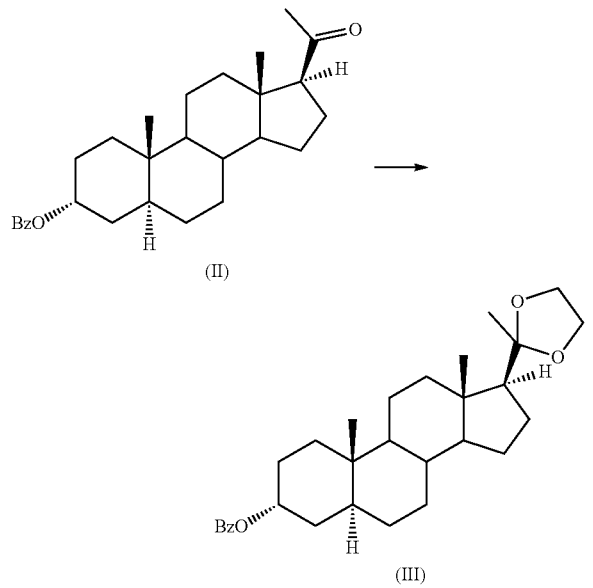

10 g of intermediate (II), obtained as described in Example 2, were dissolved in 150 ml of toluene under nitrogen flow. Ethylene glycol (26.5 ml), triethylorthoformate (25.2 ml) and p-toluenesulfonic acid (0.36 g) were added. The mixture was brought to reflux temperature (105-110° C.) and maintained under stirring for 2 hours. A TLC check was carried out, confirming the completion of the reaction (disappearance of the starting compound); the TLC check was carried out under the following conditions:

start: in CH$_2$Cl$_2$;
sample: reaction mixture in NaHCO$_3$+toluene;
eluent: toluene/isopropyl acetate 97/3; sheet: HPTLC;
detector: UV/phosphomolybdic cerium.

The reaction mixture was cooled to 10° C. and poured onto a 4% NaHCO$_3$ aqueous solution, pre-cooled at T<5° C. The system was maintained under stirring for 10 minutes, the phases were separated and the aqueous phase was re-extracted with 20 ml of toluene. The organic phases were reunited and washed with water. The solvent was removed under vacuum, obtaining 13.4 g of raw intermediate (III) (white solid).

A 5.2 g portion of raw intermediate (III) was suspended in 15.6 ml of ethyl acetate and refluxed for 5 minutes. The suspension was cooled by maintaining it at 0° C. for 1 h, and then filtered on büchner funnel by washing with ethyl acetate. The procedure was repeated two more times, obtaining, after drying at constant weight (T=50° C. and reduced P), 4.1 g of pure intermediate (III) (white solid).

Analysis of Intermediate (III):

$^1$H-NMR, CDCl$_3$: 8.07 (2H, dd, J=1.4-8.5 Hz, aromatic H); 7.56 (1H, t, J=7.3 aromatic H); 7.46 (2H, t, J=7.5 Hz, aromatic H); 5.29-5.27 (1H, m, H-3); 4.01-3.85 (4H, m, OCH$_2$CH$_2$O); 2.04 (1H, dt, J=3-11.9, H-17); 1.88-0.76 (22H, m); 1.302 (3H, s, H-21); 0.847 (3H, s, CH$_3$); 0.768 (3H, s, CH$_3$);

$^{13}$C-NMR, CDCl$_3$: 165.92 (C=O); 132.69 (aromatic CH); 131.15 (aromatic C); 129.53 (2 aromatic CH); 128.32 (2 aromatic CH); 111.97 (C, O—C—O); 70.72 (CH, C-3); 65.25 (OCH$_2$); 63.17 (OCH$_2$); 58.37 (CH); 56.39 (CH); 54.33 (CH); 42.02 (C); 40.44 (CH); 39.63 (CH$_2$); 35.90 (C); 34.95 (CH); 33.19 (CH$_2$); 33.00 (CH); 31.83 (CH$_2$); 28.37 (CH$_2$); 26.30 (CH$_2$); 24.59 (CH$_3$, C-21); 23.69 (CH$_2$); 22.88 (CH$_2$); 20.62 (CH$_2$); 13.05 (CH$_3$); 11.43 (CH$_3$);

Mass: 466 (M$^+$).

Analysis 17a Isomer of Intermediate (III):

$^1$H-NMR: the 17α isomer has the following characteristic signals: 1.323 (3H, s, H-21); 0.837 (3H, s, CH$_3$); 0.813 (3H, s, CH$_3$).

Example 9

This example relates to step 4) of the process of the invention, in the case X=O and R=ethylene, —CH$_2$—CH$_2$—.

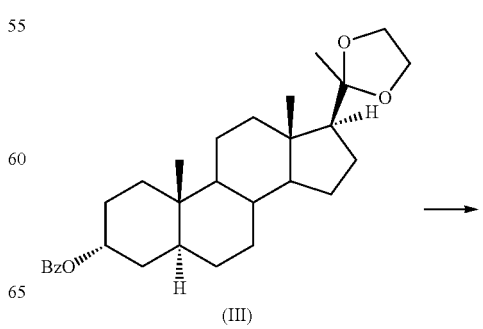

-continued

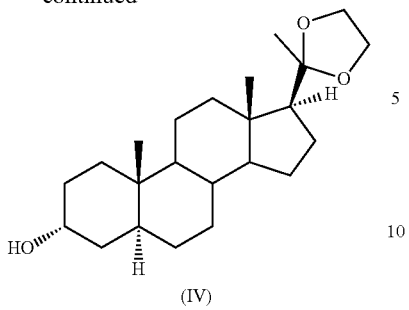

(IV)

3.2 g of ketal benzoate, obtained as described in Example 8, were suspended in 80 ml of methanol, then 6.8 g of NaOH were added. The reaction mixture was brought under reflux (65° C.) for 16 h without noticing any dissolution. A TLC check was carried out, verifying the completion of the reaction (disappearance of the starting product). The TLC check was carried out under the following conditions:
start: in $CH_2Cl_2$;
sample: reaction mixture in THF;
eluent: toluene/isopropyl acetate 6/4; sheet: TLC;
detector: UV/phosphomolybdic cerium.

The reaction mixture was cooled to 25° C. and 100 ml of water were added. The solvent was removed under vacuum at 45° C. The reaction mixture was extracted with DCM, then the organic phase was washed with water until neutral pH was reached. The organic fraction was concentrated under reduced pressure, obtaining 2.6 g of intermediate (IV) as a white solid, of suitable quality for the continuation of the synthesis.

Analysis of Intermediate (IV):

$^1$H-NMR, $CDCl_3$: 4.04 (1H, m, H-3); 4.04-3.83 (4H, m, $OCH_2CH_2O$); 2.015 (1H, dt, J=3.2-11.9, H-17); 1.82-0.72 (23H, m); 1.293 (3H, s, H-21); 0.780 (3H, s, $CH_3$); 0.751 (3H, s, $CH_3$);

$^{13}$C-NMR, $CDCl_3$: 112.00 (C, O—C—O); 66.59 (CH, C-3); 65.23 ($OCH_2$); 63.19 ($OCH_2$); 58.31 (CH); 56.41 (CH); 54.31 (CH); 42.01 (C); 39.66 ($CH_2$); 39.14 (CH); 36.10 (C); 35.87 ($CH_2$); 34.97 (CH); 32.16 ($CH_2$); 31.91 ($CH_2$); 29.00 ($CH_2$); 28.55 ($CH_2$); 24.58 ($CH_3$, C-21); 23.70 ($CH_2$); 22.88 ($CH_2$); 20.56 ($CH_2$); 13.07 ($CH_3$); 11.20 ($CH_3$);

Mass: 362 (M$^+$).

Analysis of 17α Isomer of Intermediate (IV):
The 17α isomer has the following characteristic signals: 1.300 (3H, s, H-21); 0.792 (3H, s, $CH_3$); 0.772 (3H, s, $CH_3$).

Example 10

This example relates to step 5) of the process of the invention starting from a ketal.

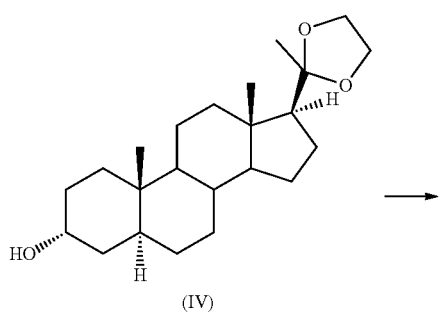

(IV) →

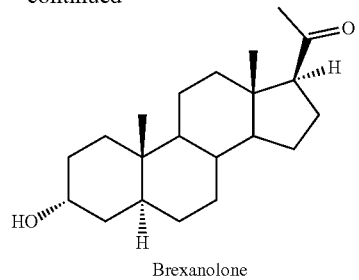

Brexanolone 1.5 g of intermediate (IV) obtained following the procedure of Example 9 were put under stirring with 22.5 ml of anhydrous acetone and 105 mg of iodine. The mixture was brought under reflux (T=58° C.) obtaining, after 10 minutes of stirring under reflux, a clear solution. A TLC check confirmed the completion of the reaction. The TLC check was carried out under the following conditions:
start: in $CH_2Cl_2$;
sample: reaction mixture diluted in acetone;
eluent: toluene/isopropyl acetate 6/4; sheet: TLC;
detector: UV/phosphomolybdic cerium.

The acetone was removed by distilling it at reduced P and the residue was taken up with DCM (50 ml). The organic phase was first washed with a 5% aqueous solution of sodium thiosulphate and then with water. The organic phase was then dry concentrated at reduced P, obtaining 1.25 g of raw brexanolone.

The HPLC analysis, performed on the raw brexanolone thus obtained, without any further purification, showed that the product contains an amount of 17α isomer equal to 0.29%.

1.0 g of the previously obtained sample was completely dissolved under reflux with 7 ml of isopropyl acetate, cooled to 0° C. for 1 h and finally filtered. The solid was dried at 50° C. obtaining 0.9 g of pure brexanolone which, analysed by HPLC, contain an amount of 17a isomer equal to 0.10%.

Example 11 (Comparative)

This example refers to the deprotection of a ketal to form brexanolone under conditions other than those of the invention.

0.1 g of intermediate (IV) obtained as described in Example 9 were loaded into a flask under nitrogen. DCM (1.1 ml) and methanol (0.7 ml) were added; no complete dissolution was observed. $NaHCO_3$ (0.096 g) was added. Then $I_2$ (0.112 g) was added and the mixture was maintained under stirring at 25° C. for 20 h, then the mixture was progressively brought to 40° C. during 6 h checking the progress of the reaction by TLC. The mixture was cooled to 0° C., and the reaction was quenched by dripping on the reaction mixture a solution of sodium thiosulfate (0.25 g) in water (5 ml) maintaining the temperature below 10° C. The mixture was brought to 25° C. and the suspension filtered on a dicalite panel, washing the solid on the filter with DCM at 35° C. The phases were separated, the aqueous phase was extracted with DCM. The organic phases were reunited and washed with water. The solvent was eliminated by evaporation at reduced pressure with rotavapor, obtaining 0.09 g of brexanolone the epimer content of which is equal to 0.7%.

Example 12

40 mg of intermediate (IV) obtained following the procedure of Example 9 were put under stirring with 0.8 ml of $CH_2Cl_2$ and 0.081 ml of acetone. 0.7 mg of iodine was added. The mixture was stirred at 25° C. and after 10 minutes it was confirmed with a TLC check that the reaction was completed (disappearance of the starting compound). The mixture was maintained under stirring for another 18 hours at 25° C. to test the stability of the product. Upon TLC check the formation of degradation products was not noted. The organic phase was first washed with a 5% aqueous solution of sodium thiosulphate and then with water. The organic phase was dry concentrated at reduced P obtaining 36 mg of brexanolone.

The HPLC analysis, performed on the brexanolone thus obtained, without any further purification, showed that the product contains an amount of 17a epimer equal to 0.04%.

Example 13

40 mg of intermediate (IV) obtained following the procedure of Example 9 were put under stirring with 0.8 ml of $CH_2Cl_2$ and 0.081 ml of acetone. 2.8 mg of iodine were added. The mixture was stirred at 0° C. and after 15 minutes with a TLC check it was confirmed that the reaction was completed (disappearance of the starting compound). The organic phase was first washed with a 5% aqueous solution of sodium thiosulphate and then with water. The organic phase was dry concentrated at reduced P obtaining 35 mg of brexanolone.

The HPLC analysis, performed on the brexanolone thus obtained, without any further purification, showed that the product contains an amount of 17a epimer equal to 0.09%.

The invention claimed is:

1. A method for the preparation of 3α-hydroxy-5α-pregnan-20-one (brexanolone) which consists in the deprotection of a cyclic ketal or a cyclic thioketal thereof of general formula (IV) with the use of iodine in an organic solvent, according to the reaction scheme:

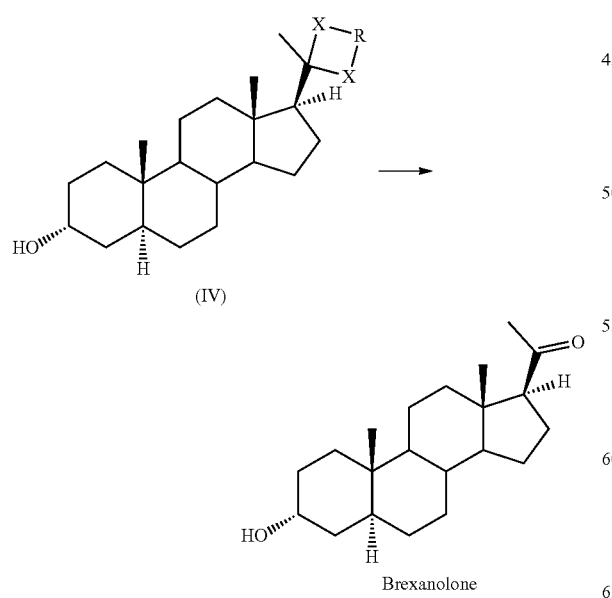

(IV)

Brexanolone wherein is X=O (oxygen) in the case of ketal and X=S (sulfur) in the case of thioketal, and R is a radical selected among ethylene (—$CH_2$—$CH_2$—), propylene (—$CH_2$—$CH_2$—$CH_2$—) and 2,2-dimethylpropylene (—$CH_2$—$C(CH_3)_2$—$CH_2$—).

2. The method according to claim 1, wherein when is X=O, the ketal of formula (IV) is hydrolysed in a neutral environment, using iodine in anhydrous acetone or in a water-free mixture of dichloromethane and acetone, operating at a temperature between −5° C. and the reflux temperature of the reaction mixture.

3. The method according to claim 2, wherein iodine is used in an amount between 1 and 10% by weight with respect to the amount of ketal (IV).

4. The method according to claim 1, wherein when is X=S, the thioketal of formula (IV) is hydrolysed with iodine in an organic solvent at a temperature between −30 and 20° C. in the presence of a solid inorganic base.

5. The method according to claim 4, wherein said organic solvent is selected among dichloromethane, methanol or a mixture thereof, and the solid inorganic base is selected among sodium carbonate, lithium carbonate, potassium carbonate, calcium carbonate, sodium bicarbonate, lithium bicarbonate and potassium bicarbonate, and the reaction is carried out at a temperature between −25 and −5° C. for a period of time between 1 and 18 hours.

6. A process for the synthesis of 3α-hydroxy-5α-pregnan-20-one (brexanolone) comprising the following steps:

1) Catalytic hydrogenation of the double bond in position 5,6 of pregnenolone in order to obtain the corresponding saturated steroid of formula (I), with the hydrogen atom in position 5 of the steroid skeleton in a spatial arrangement α:

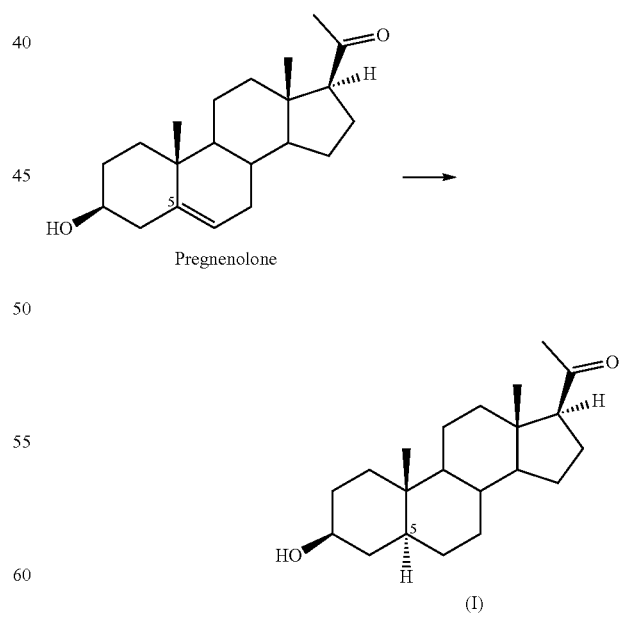

Pregnenolone (I)

2) Inversion of the spatial orientation of the hydroxyl in position 3 of the compound of formula (I) which, at the end of the reaction, is protected as benzoic ester, obtaining the compound of formula (II):

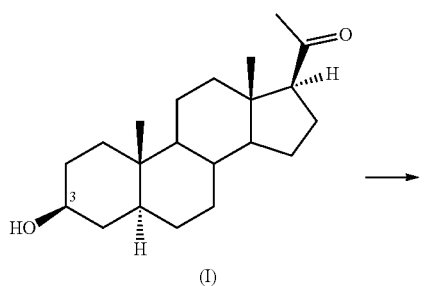

(I)

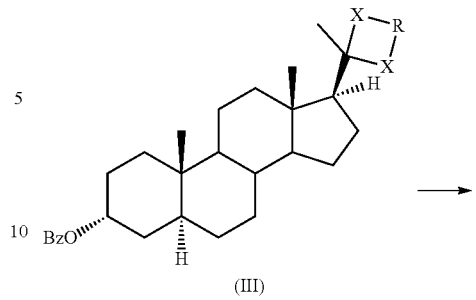

(III)

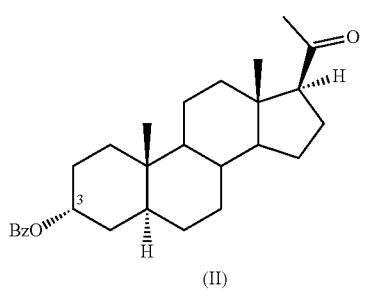

(II)

3) Protection of the carbonyl in position 20 of the compound (II) as ketal or thioketal, obtaining the compound of general formula (III), wherein is X=O or X=S and R is a radical selected among ethylene (—CH$_2$—CH$_2$—), propylene (—CH$_2$—CH$_2$—CH$_2$—) and 2,2-dimethylpropylene (—CH$_2$—C(CH$_3$)$_2$—CH$_2$—):

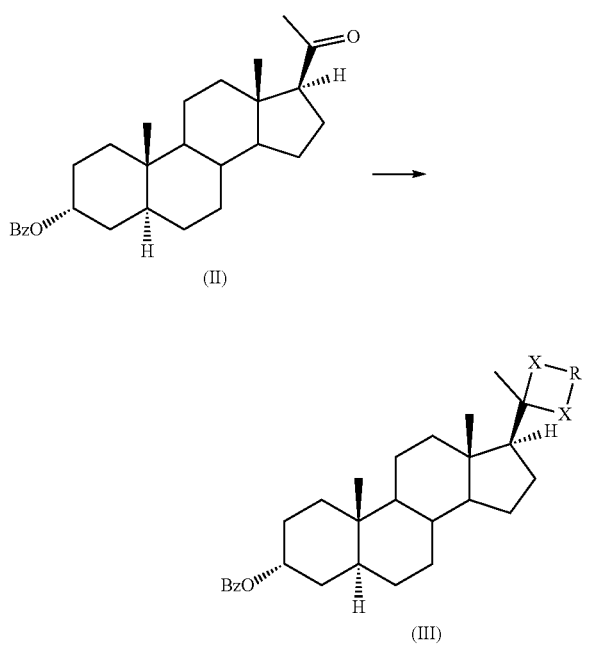

4) Hydrolysis of the benzoic ester of compound (III) obtaining the compound of general formula (IV), wherein X and R have the meanings reported above:

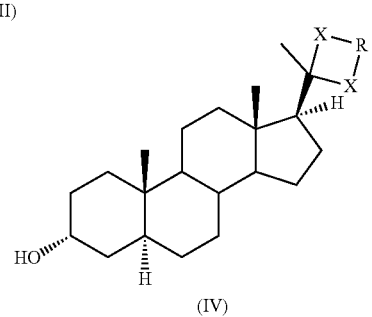

(IV)

5) Deprotection of the position 20 of the compound of general formula (IV) obtaining brexanolone according to the method of claim 1:

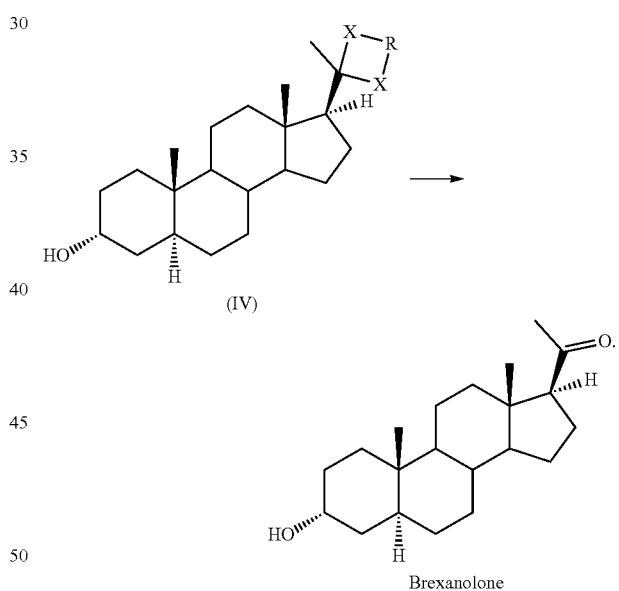

Brexanolone

7. The process according to claim 6, wherein step 1) is carried out using palladium supported on carbon (Pd/C) at 5% as hydrogenation catalyst in an amount of 5% with respect to the weight of pregnenolone, at a hydrogen pressure between 2 and 5 bar, in tetrahydrofuran (THF) as a solvent, at a temperature between 35 and 45° C. and for a time between 3 and 7 hours.

8. The process according to claim 6, wherein step 2) is carried out by reacting compound (I) with benzoic acid in tetrahydrofuran (THF) as the solvent and allowing to react for a time between 14 and 20 hours with triphenylphosphine and diisopropyl azodicarboxylate (DIAD) at a temperature between 15 and 25° C.

9. The process according to claim 6, wherein in step 3) the carbonyl in position 20 of compound (II) is protected as ketal, reacting under reflux a mixture of compound (II) with toluene, a glycol selected among ethylene glycol, propylene glycol and 2,2-dimethylpropylene glycol, triethyl orthoformate and p-toluenesulfonic acid.

10. The process according to claim 6, wherein in step 3) the carbonyl in position 20 of compound (II) is protected as thioketal, reacting compound (II) with etanedithiol or propanedithiol in a solvent selected among acetic acid, dichloromethane ($CH_2Cl_2$), ethyl ether, acetonitrile, tetrahydrofuran (THF) and 1,2-dichloroethane, in the presence of a catalyst selected among boron trifluoride etherate ($BF_3 \cdot Et_2O$), zinc iodide ($ZnI_2$), titanium tetrachloride ($TiCl_4$), tin dichloride ($SnCl_2$), magnesium iodide ($MgI_2$), lithium perchlorate ($LiClO_4$), aluminum trifluoromethanesulfonate (aluminum triflate, $Al(OTf)_3$), lithium tetrafluoroborate ($LiBF_4$) and cobalt dichloride ($CoCl_2$), at a temperature in the range between 15 and 45° C. and for a time between 8 and 36 hours.

11. The process according to claim 6, wherein step 4) is carried out by refluxing compound (III) in methanol for a period between 20 and 28 hours in the presence of sodium hydroxide.

\* \* \* \* \*